United States Patent [19]

Cohen et al.

[11] Patent Number: 5,443,515

[45] Date of Patent: Aug. 22, 1995

[54] VERTEBRAL BODY PROSTHETIC IMPLANT WITH SLIDABLY POSITIONABLE STABILIZING MEMBER

[75] Inventors: Robert C. Cohen, Rockaway Township; Robert G. Averill, Ringwood, both of N.J.

[73] Assignee: Implex Corporation, Allendale, N.J.

[21] Appl. No.: 187,090

[22] Filed: Jan. 26, 1994

[51] Int. Cl.$^6$ ............................................. A61F 2/44
[52] U.S. Cl. ................................. 623/17; 606/61
[58] Field of Search .................... 623/17; 606/61, 71

[56] References Cited

U.S. PATENT DOCUMENTS

| | | | |
|---|---|---|---|
| 3,848,601 | 11/1974 | Ma et al. | 128/305 |
| 4,401,112 | 8/1983 | Rezaian | 128/92 |
| 4,501,269 | 2/1985 | Bagby | 128/92 |
| 4,553,273 | 11/1985 | Wu | 623/18 |
| 4,599,086 | 7/1986 | Doty | 623/17 |
| 4,636,217 | 1/1987 | Ogilvie et al. | 623/17 |
| 4,655,777 | 4/1987 | Dunn et al. | 623/16 |
| 4,673,409 | 6/1987 | Van Kampen | 623/23 |
| 4,820,305 | 4/1989 | Harms et al. | 623/16 |
| 4,878,915 | 11/1989 | Brantigan | 623/17 |
| 4,892,545 | 1/1990 | Day et al. | 623/17 |
| 4,932,975 | 6/1990 | Main et al. | 623/17 |
| 4,955,908 | 9/1990 | Frey et al. | 623/17 |
| 4,957,819 | 9/1990 | Kawahara et al. | 428/547 |
| 4,961,740 | 10/1990 | Ray et al. | 606/61 |
| 4,978,358 | 12/1990 | Bobyn | 623/23 |
| 5,015,247 | 5/1991 | Michelson | 606/61 |
| 5,026,373 | 6/1991 | Ray et al. | 606/61 |
| 5,049,155 | 9/1991 | Bruchman et al. | 623/17 |
| 5,055,104 | 10/1991 | Ray | 606/61 |
| 5,062,850 | 11/1991 | MacMillan et al. | 623/17 |
| 5,071,437 | 12/1991 | Steffee | 623/17 |
| 5,104,410 | 4/1992 | Chowdhary | 623/11 |
| 5,129,903 | 7/1992 | Luhr et al. | 606/71 |
| 5,180,381 | 1/1993 | Aust et al. | 606/61 |
| 5,192,327 | 3/1993 | Brantigan | 623/17 |
| 5,198,308 | 3/1993 | Shetty et al. | 428/608 |
| 5,201,766 | 3/1993 | Georgette | 623/16 |
| 5,211,661 | 5/1993 | Shinjou et al. | 623/16 |
| 5,236,457 | 8/1993 | Devanathan | 623/16 |
| 5,236,460 | 8/1993 | Barber | 623/17 |

FOREIGN PATENT DOCUMENTS

| | | | |
|---|---|---|---|
| 0179695 | 4/1986 | European Pat. Off. | 623/17 |
| 405015548 | 1/1993 | Japan | 623/17 |
| 829104 | 5/1981 | U.S.S.R. | 606/61 |
| 2004218 | 12/1993 | U.S.S.R. | 623/17 |
| 1107854 | 8/1994 | U.S.S.R. | 623/17 |

*Primary Examiner*—David Isabella
*Assistant Examiner*—Laura Fossum
*Attorney, Agent, or Firm*—Arthur L. Plevy

[57] ABSTRACT

A spinal stabilization device positionable between neighboring vertebral bodies to provide rigid internal fixation thereof and thus stabilize a spinal column which has been rendered unstable by disease or injury. The device includes a vertebral body prosthesis dimensioned to act as a replacement for a damaged vertebral body and associated discs which have been removed. Once implanted, the prosthesis provides direct mechanical stability and preserves the original spacing between the neighboring vertebral bodies, thereby preventing nerve damage and ensuring proper tensioning of the soft tissue surrounding the implantation site. To facilitate long-lasting bony fixation, the prosthetic implant is fabricated from a rigid, tantalum foam material. The open surface porosity at the interface between the adjacent vertebral bodies and the prosthesis enhances the opportunity for axial bone growth to take place, and ultimately, for fusion of the adjacent vertebral bodies to occur. External axial grooves may also be provided to further accommodate bone ingrowth or adjunct stabilizing members.

20 Claims, 5 Drawing Sheets

VERTEBRAL BODY PROSTHETIC IMPLANT WITH SLIDABLY POSITIONABLE STABILIZING MEMBER

BACKGROUND OF THE INVENTION

The present invention relates to devices and methods for stabilizing the spine. It more particularly relates to stabilization of a spinal column that has been rendered unstable by any disease such as a tumor, infection, or congenital anomalies affecting the vertebral bodies or associated supporting structures.

Preservation of neurologic function and relief of pain are the primary goals of treatment of diseases affecting the vertebral bodies. Oftentimes such diseases themselves destroy the vertebral body or the surgical treatment necessitates its resection. As a result of the loss of bony support, the vertebral column is unstable causing pain, progressive neurologic deterioration, and physical deformity of the back. In such cases stabilization of the spinal column by an anterior surgical approach may be required.

A common technique utilized for stabilization of the anterior spine is to fill the space of the resected vertebral bodies with methylmethacrylate or other similar plastic or plastic-like polymers. Difficulties encountered with this method include the inability to bond securely the plastic material to tissue or bone, the injurious release of heat into the surrounding tissue because of the exothermic chemical reaction required for polymerization of the plastic, potential stress fractures of the plastic caused by mechanical forces related to weight bearing, and the need to mold the plastic to the appropriate size which is often technically cumbersome and difficult. Although metallic pins or struts are often used to reinforce the methylmethacrylate, they do not provide adequate mechanical or torsional stability.

Attempts at spinal stabilization have also been performed utilizing a variety of metal pins and struts as mentioned previously. One common method is to penetrate adjacent vertebral bodies with Steinmann pins and then surround the pins with methylmethacrylate. Many technical problems are associated with this procedure including (1) those difficulties specially related to methylmethacrylate; (2) the inability to maintain distraction adequately while polymerization of the plastic is taking place; (3) the inability to adequately place the pins because of space restrictions; and (4) the fracture of the pins resulting in loss of stability and possible movements of the methylmethacrylate.

Another common method of anterior spine stabilization utilizes bone to act as a replacement for the vertebral body after its removal. Bone of the iliac crest, fibula, or tissue-banked cadaver bone has been used. Typically, the bone material is introduced into a hollow place holder or "cage" positioned between adjacent vertebrae to be fused. Reference is made, for example, to U.S. Pat. No. 4,820,305 entitled PLACE HOLDER, IN PARTICULAR FOR A VERTEBRA BODY and issued to Harms et al on Apr. 11, 1989. In that patent, there is disclosed a mesh-like cage having a diameter and axial length selected so that the cage fits between the remaining vertebrae and maintains the original separation therebetween. The ends of the cage define teeth which are intended to engage the end plates of the superior and inferior vertebral bodies and reduce the effects of torsion. Several limitations of this technique exist, however. Immediate stabilization is not possible because adequate bony fusion requires three to six months. When radiations therapy and/or chemotherapy are required to treat the primary disease process affecting the spine, the implanted bone graft often does not survive and this results in further spinal instability secondary to resorption of the bone graft.

Yet another method for anterior spinal stabilization utilizes one or two metal rods attached by screws to the lateral aspect of the adjacent vertebral bodies. This procedure was first described by Dunn in 1980. There are two primary limitations of this procedure. First, it cannot be used in certain areas of the spine because of the vital structures adjacent to the lateral aspect of the vertebral body. Second, the device is inherently weak since mechanical stresses are maximally exerted at the site of attachment of the device to the vertebral body by small metal screws.

Metal rod distraction utilizing Harrington or Knodt rods, with or without methylmethacrylate, is another method to stabilize the spine via the anterior approach. This procedure was described by Harrington in 1976. One or more rods are typically attached via hooks to the anterior portion of the vertebral body and they can then be covered with methylmethacrylate to further secure them in place. The major disadvantages of this technique is the slippage of the stabilizing rods secondary to the mechanical forces generated by spine movement. These forces are greatest at the site of hook insertion and may cause fracture of the vertebral body to which it is attached. Moreover, involvement of the adjacent vertebral bodies with disease may weaken the bone at the site of hook insertion and lead to migration of the rods with resultant collapse of the spinal column.

Of the drawbacks discussed in connection with the above techniques, perhaps the most inconvenient for the patient is the reliance upon external fixation for the extended periods of time required for vertebral fusion. As such, more recent efforts have been directed to the development of inert prosthetic implants to replace the resected vertebral body and adjacent discs. In U.S. Pat. No. 4,932,975 entitled VERTEBRAL PROSTHESIS and issued to Main et al on Jun. 12, 1990, for example, there is described an implant which comprises a pair of rigid housings joined by a connecting structure that is operable to shift the housings apart into supporting engagement with the healthy vertebral bodies adjacent the resected vertebral body. Anchoring pins project from each respective housing and into the end plate of a corresponding vertebral body. A primary disadvantage of the implant described by Main et al, however, is that it does not adequately provide for bone ingrowth and relies substantially on the anchoring pins to maintain the prosthesis in position.

Reference is also made to U.S. Pat. No. 5,062,850 to McMillan et al entitled AXIALLY-FIXED VERTEBRAL BODY PROSTHESIS AND METHOD OF FIXATION and issued on Nov. 5, 1991. McMillan et al disclose a vertebral body prosthetic device which comprises upper and lower end plates separated by a plurality of support columns or posts. The plates are affixed to neighboring vertebral bodies via axially oriented screws. Bone is packed between the plates and across the sides of the device after it has been fixed into position to facilitate eventual bone ingrowth. One drawback of the McMillan et al device is that if the bone material placed within the device loosens, it may become displaced and irritate adjacent tissue. Moreover, like the device taught by Main et al, the McMillan et al device relies largely upon the axial screws to provide fixation of the implant. Instead of extending axially between the entire area of the vertebral body end surfaces, bone ingrowth is limited to gradual encasing of the implant.

In U.S. Pat. No. 5,192,327 entitled SURGICAL PROSTHETIC IMPLANT FOR VERTEBRAE and issued to Brantigan on Mar. 9, 1993, there is disclosed yet another vertebral body prosthesis. Brantigan discloses a prosthetic implant having an oval cross section and comprised of a plurality of modular segments. The edges of the segments have grooves such that individual sections may be interdigitated to achieve a desired length. The individual sections are held together by a bar member that extends axially within the interior bore of each segment and that divides the interior bore into two central apertures. Unlike the prostheses disclosed by Main et al and McMillan et al, the Brantigan prosthesis, does provide for the eventual uninterrupted, axial ingrowth of bone between the end plates of the vertebra surrounding, the resected vertebral body. However, Brantigan relies solely on the peripheral edges of the hollow implant to provide the initial fixation. As such, the device is initially vulnerable to torsional displacement or lateral shifting.

Accordingly, the principal object of the present invention is to provide a novel device and method for stabilizing the spinal column following the resection of a vertebral body and adjacent discs but without the shortcomings and disadvantages of the prior methods as set forth above.

SUMMARY OF THE INVENTION

The present invention relates to a rigid prosthetic implant for providing a long-term replacement of a vertebral body that is damaged. The first function of the implant is to serve as a spacer for the maintenance of spinal alignment and soft tissue tensioning following removal of a portion of a diseased spine. The prosthesis will maintain the height of the anterior spinal column, thus preventing deformities from occurring. Its second function is to provide an element of rigid internal fixation so that bone fusion can take place between the neighboring vertebral bodies and about the implant itself. The device is implanted into the spinal column after ablation of the affected anterior vertebral body and neighboring discs.

The height of the implant is selected to be compatible with the height of the anterior portion of a cervical, thoracic, or lumbar vertebral body and corresponding discs that it is to replace. Accordingly, the implant is configured to closely approximate the cross sectional profile of the cervical, thoracic, or lumbar vertebral body it replaces, but is slightly smaller. The slightly smaller geometry allows for proper implant placement if bone and soft tissue are left behind due to limited exposure and sensitivity of the operative site. Moreover, a smaller cross sectional profile ensures that there are no substantial protrusions beyond the anterior margins of the anterior vertebral column and only slight lateral protrusion, thereby minimizing irritation to surrounding tissue. Preferably, the body has a cross sectional profile that is dimensioned to closely approximate the cross section of the anterior vertebrae but is slightly smaller. The superior and inferior side surfaces of the implant are formed with grooves to resist rotational and translational forces.

In accordance with a preferred embodiment of the present invention, a completely porous prosthetic structure is fabricated from a tantalum open-celled lattice material. Using such a material, a prosthetic structure having a bulk volume porosity exceeding 80% and requiring no substrate support may be constructed. In order to provide a suitable framework for bone ingrowth, the bulk volume porosity of the material should not be substantially lower than 50%. In fact, a bulk volume porosity of at least 60% is preferred. The high degree of surface and volumetric porosity of an implant constructed in accordance with this embodiment allows the ingrowth of bone in an axial direction over the entire end plate surface area of the adjacent vertebral bodies, thereby providing bony fixation or, if necessary, allowing cement interdigitation. To further accommodate bony ingrowth, thoracic and lumbar implants may be provided with longitudinal, internally tapered channels which can be packed with bone graft material prior to or during implantation. The taper channels provide for the retaining of the graft.

To further enhance initial resistance to translational and rotational forces during and immediately after implantation, at least one stabilizing member slidably disposed within a lateral one of the longitudinal channels may be utilized to secure the prosthesis to the adjacent vertebral bodies.

In accordance with a preferred embodiment, each stabilizing member includes an axially extending plate dimensioned and arranged to rest on the outside surface of a neighboring vertebral body. The axially extending plate contains an aperture to accommodate a bone screw which screw can be transcortically screwed into the bone. In the alternate embodiment, the stabilizing member is retained at a desired position relative to a vertebral body by a locking screw which extends through that portion of the stabilizing member disposed within the groove and, upon tightening, into the implant itself.

In accordance with an alternate embodiment, each stabilizing member includes an axially extending pin which is adapted to penetrate the hard cortex bone of a neighboring vertebra. The stabilizing member is impacted upon until the pin seats in the vertebral body end plate.

Surgical insertion of the implant is simplified in that it requires relatively small access openings through the patient's body, and once secured, provides rigidity that is limited only by the bone structure of the adjacent vertebrae to which the implant is affixed. Because the implant is rigidly held in place, stabilization is immediate and bony healing can more predictably extend into the highly porous structure.

DETAILED DESCRIPTION OF THE INVENTION

Figure 1:
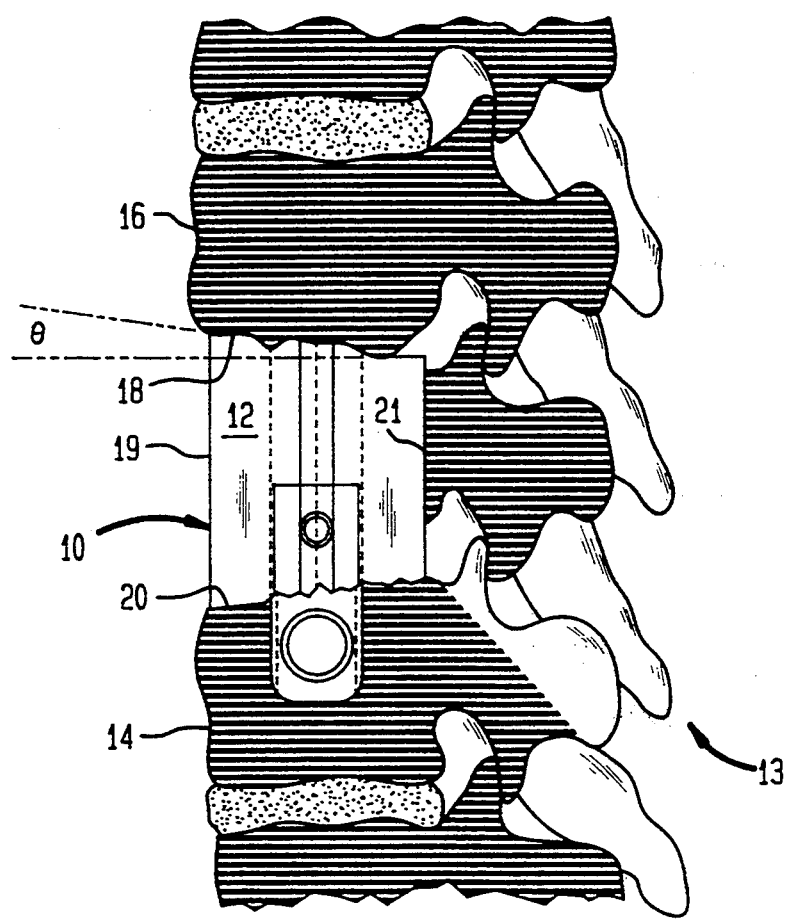
FIG. 1 is a side elevation view of a preferred embodiment of a prosthetic vertebral body with stabilizing members shown secured to the spinal column of a patient.

A vertebral body prosthetic implant according to the present invention is identified generally by numeral 10 in FIG. 1. As seen in FIG. 1, the implant 10 approximates the height dimension of one human vertebral body and two adjacent vertebral discs within a spinal column generally indicated at 13. The implant is positioned, as shown, between a lower vertebra 14 and an upper vertebra 16. Although the superior and inferior surfaces of the implant may be parallel to one another, it is also possible to configure them to correspond to the curvature of the spine at the implantation site. For example, in the illustrative embodiment depicted in FIG. 1 the superior side surface 18 and inferior side surface 20 of implant 10 are slightly tapered from the anterior surface portion 19 toward the posterior surface portion 21 to accommodate implantation in the lumbar region of the spine. Although an angle of inclination θ of 5° from the horizontal will generally be acceptable for lumbar region implantations, it will be readily appreciated by those skilled in this art that higher or lower angles of inclination may be employed if it is desired to more closely accommodate the specific geometry of the neighboring vertebra of a particular patient. Alternately, for implantation in the thoracic region of the spine, neither of the side surfaces of the implant need be tapered.

Implant 10 may be made of any bio-compatible material, including metal (e.g. stainless steel, cobalt chrome alloy, and titanium) and ceramics. Preferably, however, the material is porous. A porous structure in accordance with the present invention may be formed by any of a variety of known methods. It may, for example, include flame or plasma sprayed titanium, sintered metal beads, sintered ceramics, or other suitable materials. Preferably, however, a completely open-celled lattice or foam structure of tantalum is utilized. This material comprises a skeleton of vitreous carbon that initially defines a network of interconnecting pores. It will be readily appreciated by those skilled in the art that the porosity of the final product is dependent upon the size and spacing of the pores in the carbon skeleton. Through a chemical vapor deposition process, tantalum is infiltrated into and about the carbon skeleton. In addition to possessing the desired properties of rigidity, strength, and bio-compatibility, the porous structure of the tantalum foam material has been found to facilitate the rapid ingrowth of bone between neighboring vertebral bodies as 14 and 16. In order to provide a suitable framework for such bone ingrowth, the bulk volume porosity of the material should not be substantially lower than 50%. In fact, a bulk volume porosity of at least 60% is preferred. However, although a porous structure is preferred in order to facilitate bone ingrowth, it is also contemplated that non-porous structures fabricated from the classes of materials described above may be utilized as well.

Figure 2:
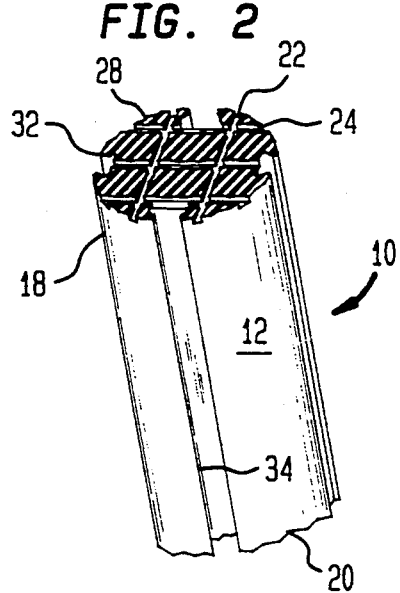
FIG. 2 is a perspective view of the preferred embodiment of the prosthetic vertebral body.
Figure 3:
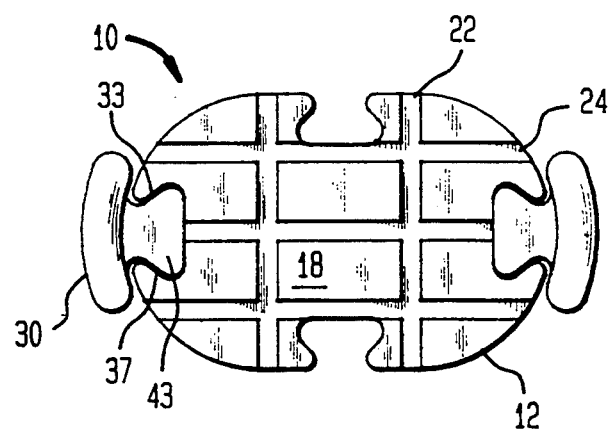
FIG. 3 is a plan view showing an end surface portion of the prosthetic vertebral body in conjunction with two stabilizing members.

With continuing reference to FIG. 1, it will be seen that the superior and inferior surfaces of implant 10 engage respective surfaces of neighboring vertebra 14 and 16. As indicated above, the superior and inferior side surfaces of implant 10 preferably include grooves or a similar embossment that resists rotational and translational forces when the implant 10 is implanted between vertebral bodies. In FIG. 2, for example, superior side surface 18 is shown as having a grid-like network of vertical and horizontal grooves, indicated generally at 22 and 24, respectively. Grooves 22 and 24 serve as anchoring points for bone ingrowth from the adjoining vertebra. Arranged within each area bounded by grooves 22 and 24 are a plurality of teeth 28 which bite into the adjoining vertebrae during implantation. Because the teeth and grooves are distributed over the entire area of end surfaces 18 and 20, the resistance of the implant to displacement from linear and torsional forces is substantially enhanced. It will therefore be apparent to those of ordinary skill in the art that with the toughened end surfaces 18 and 20 and selectively positionable stabilizing means to be described below, implant 10 provides an initial, reliable fixation while also facilitating the ingrowth of bone over the entire areas of contact between the implant and the adjacent vertebral bodies. As seen in FIG. 3, implant 10 has a cross sectional profile that is dimensioned to closely approximate the cross sectional geometry of the anterior vertebral body it replaces, but is slightly smaller.

As indicated above, teeth 28 of upper and lower surfaces 18 and 22 enhance the stability of the implant 10 by providing a means for the fixation of the implant 10 to surrounding vertebra 14, 16. Additionally, adjunct fixation of implant 10 to adjacent vertebra 14 and 16 may be performed by one or more selectively positionable stabilizing members which will now be described. It is, of course, contemplated that any suitable stabilizing structure may be used to secure the implant to the neighboring vertebral bodies, including external devices and fixation plates. With initial reference to the illustrative implant depicted in FIGS. 1–3, it will be observed that the outer surface of implant 10 defines a lateral pair and an anterior-posterior pair of opposed channels, 32 and 34, respectively. It will, of course, be appreciated that the number of channels may be modified and that these may be radially distributed in any desired manner.

As can be seen from FIG. 3, each of the channels formed within the implant have outwardly converging sidewall surfaces 35,37 that give each channel a generally dovetail-shaped profile. The converging sidewalls 35, 37 of each channel provide the channel with a configuration wherein the width of the channel at the outer surface of the implant 10 is not as wide as the width of the channel at its base within the implant 10.

Figure 4A:
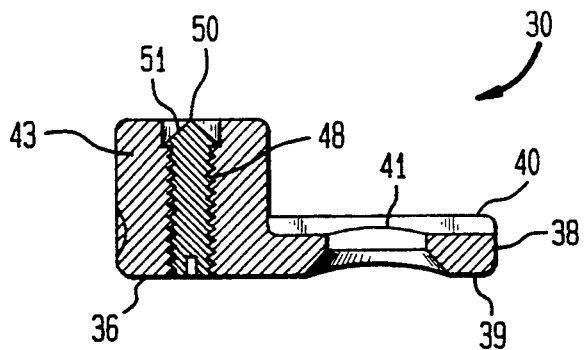
FIGS. 4A–4C are various views depicting one embodiment of a stabilizing member utilized to secure the prosthetic implant of the present invention to a neighboring vertebral body.
Figure 4B:
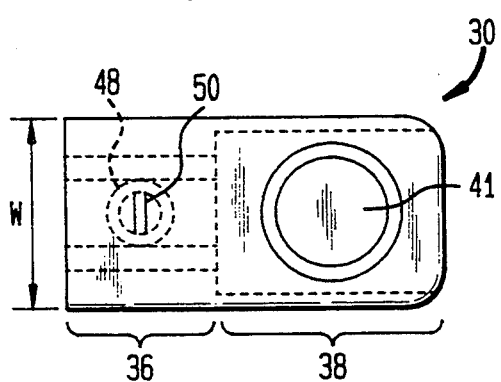
Figure 4C:
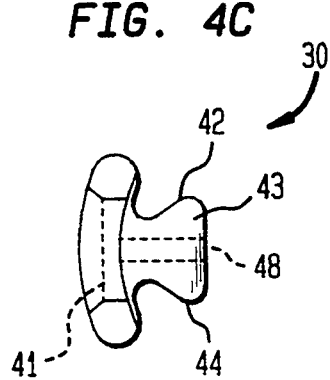

Referring to FIGS. 4A–4C a first embodiment of a stabilizing member 30 is shown that engages the channels within the implant. In the shown embodiment, each stabilizing member 30 includes a wide body portion 36 and a relative thin plate portion 38. The plate portion 38 shares the same width W as the base of the body portion 36. However, a smaller locking protrusion 43 extends from the body portion 36. The locking protrusion 43 is dimensioned to fit within the channels on the implant, wherein each locking protrusion 43 has a generally dovetail-shaped profile with diverging external surfaces 42 and 44. The slope of the diverging external surfaces 42, 44 matches the slope of the sidewalls 35,37 of the channels within the implant (see FIG. 3). However, the locking protrusion 43 is sized to be slightly smaller than the channels in the implant. As a result, the locking protrusion 43 can be slidable moved within each channel, back and forth across the length of the channel.

A threaded screw hole 48 is disposed within the body portion 36 of the stabilizing member 30. A screw 50 is threadably engaged within the screw hole 48. The screw 50 includes an enlarged pointed head 51, the purpose of which will be later described. A bore 41, having a beveled recess, is disposed within the plate portion 36 of the stabilizing member 30. As will be later described, the bore 41 is sized to accept a bone screw that joins the stabilizing member 30 to vertebral bone.

Figure 5:
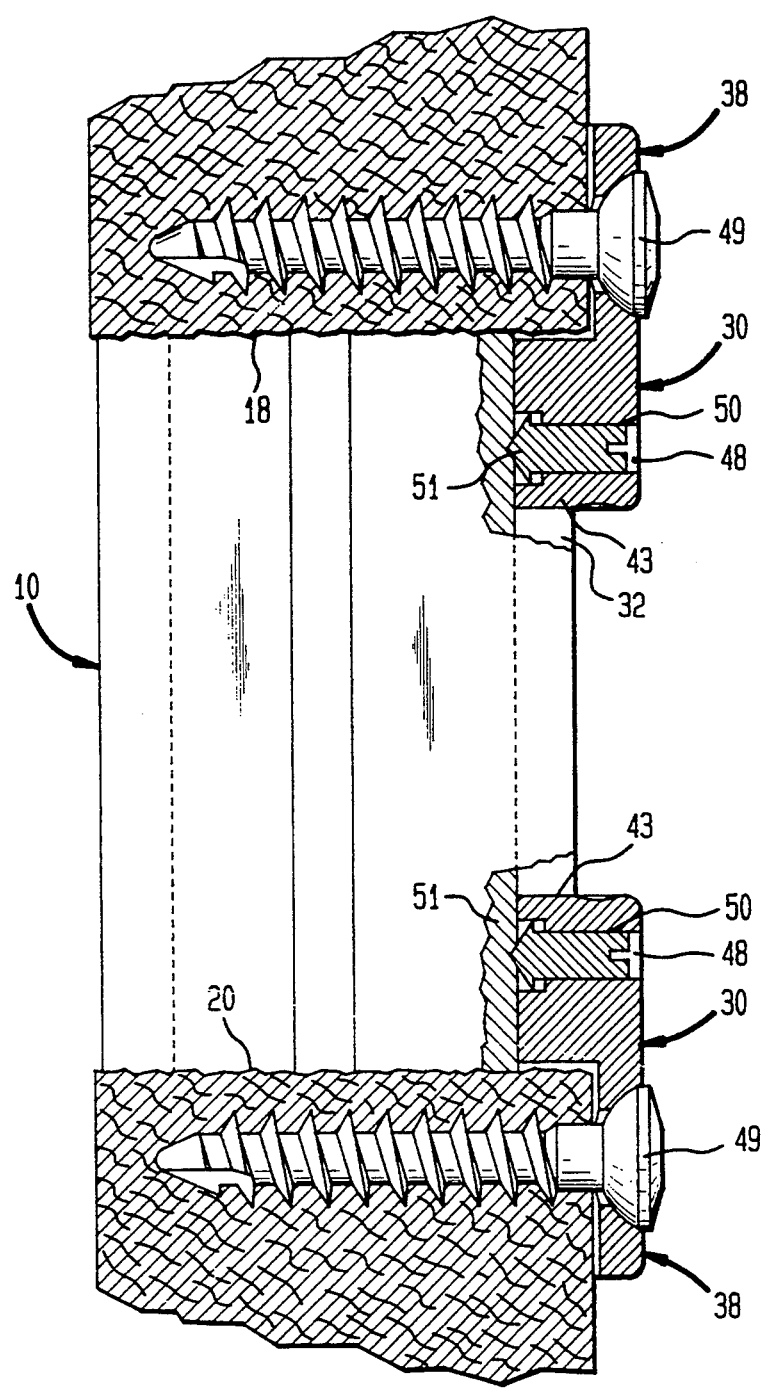
FIG. 5 is a cross-sectional view of the prosthetic vertebral body shown in FIG. 2, wherein two stabilizing members such as those shown in FIGS. 4A–4C used to secure the prosthetic vertebral body to the surrounding vertebrae.

Referring to FIG. 5, it can be seen that the stabilizing members 30 are positioned in the channels 32 that are formed within the implant 10. The generally dovetail-shaped locking protrusion 43 of each stabilizing member 30 fits within the generally dovetail-shaped channels, thereby enabling the stabilizing members 30 to slide back and forth along the length of each channel. The complimentary dovetail shape of the channels and stabilizing members 30, therefor prevent the stabilizing members 30 from laterally disengaging from the channels. (See FIG. 3)

As shown in FIG. 5, the locking protrusions 43 of the stabilizing members 30 are affixed at set positions within the channels of the implant 10, so that the plate portion 38 of each stabilizing member 30 extends beyond the implant 10 and overlaps the surrounding vertebral bone. The locking protrusion 43 of each stabilizing member 30 is anchored into a set position in the channels by the screw 50 that threadably engages the threaded screw hole 48 formed through the stabilizing member 30. By driving the screw 50 through the threaded hole 48 in the stabilizing member 30, the enlarged pointed head region 51 of each locking screw 50 is driven against the material of the implant 10. This causes the dovetail-shaped protrusion 43 of the stabilizing member 30 to bind within the channels and thereby become locked in a set position.

As has been previously described, the implant 10 is preferably made of tantalum foam. With the use of such material, it is possible to drive the pointed head region 51 of each screw 50 directly into the tantalum foam that comprises the implant 10. FIG. 5 shows the locking screws 50 driven into the material of the implant 10. As the enlarged pointed head region 51 of each screw 50 displaces the tantalum foam, the tantalum foam envelops the point of the screw, creating a custom fit between the screw and the tantalum foam. The presence of the pointed end of the screws 50 within the material of the implant, anchors the screws in place, thereby helping to further secure the stabilizing members 30 into a set position within the channels of the implant.

The attachment of the stabilizing members 30 to the implant 10 via the locking screws may be done by the surgeon at the time of the operation. However, it should be understood that the stabilizing members 30 may come preassembled to the implant from the manufacturer in standard sizes.

Regardless to where the stabilizing members 30 are assembled to the implant 10, each of the stabilizing members 30 are joined to the surrounding vertebral bone with a bone screw 49. The bone screws 49 thereby anchor the stabilizing members to the vertebral column and provide adjunct initial fixation while bone regrowth occurs.

In a preferred configuration, the diameter of the enlarged head region 51 of each of the locking screws 50 is greater than the diameter of the threaded hole 48. As a result, the locking screws 50 can not be retreated within the threaded holes 48 beyond the point where the head region 51 contacts the body of the stabilizing member 30 proximate the threaded hole 48. The locking screws 50 are sized so that the enlarged head region 51 of the screws abut against the body of the stabilizing member 30 before the opposite end of the screws 50 extend beyond the outside surface of the stabilizing member 30. Accordingly, this configuration ensures that the locking screws 50 will not unscrew from the threaded holes 48 and extend beyond the limits of the stabilizing member 30, thereby preventing any irritation, inflammation or other damage that may occur from a protruding screw.

To implant the present invention vertebral body prosthesis the neighboring vertebral bodies are first distracted as by temporarily attaching conventional distraction devices (not shown). In a standard lateral approach, the diseased vertebral body to be replaced is exposed and removed, along with the associated discs. The implant 10, along with a stabilizing member 30 positioned within at least one of the lateral channels 32, is then placed into the void left by the removal of the diseased vertebral body. It will, of course be apparent to those of ordinary skill in the art that an additional stabilizing member may be positioned within more than one channel and/or at the opposite ends of the same channel in order to enhance initial fixation. Alternatively, the stabilizing members need not be used in situations where the fixation directly between the implant and the adjacent vertebral bodies is sufficient for the needs of the patient.

The implant is placed so that it is completely within the margins of the spinal column and so that the plate portion 38 of each stabilizing member 30 may be aligned with the hard cortex a neighboring vertebral body. The distraction devices are removed to allow an end face of each neighboring vertebra to fully engage a corresponding end surface 18 or 20 of implant 10. If two stabilizing members are used, they are moved in opposite directions within the channel until the plate section 38 overlies the side of an adjacent vertebral body. The screws 50 are then tightened to lock each stabilizing members into position, provided that the stabilizing members not preassembled by the manufacturer.

The rigidity imparted to the spinal column will vary according to the status of the bone of the adjacent portions of the spinal column, and bone integrity, rather than failure of the implant itself is the limiting factor. Since no substantial residual material is left outside the margins of the anterior vertebral column, there is no interference or irritation of tissue or vessels adjacent the spinal column. The inserted implant provides immediate stability and permits bony healing to take place between the remaining vertebrae. When the implant is constructed of porous material in accordance with the preferred embodiment, the ingrowth of bone can continue uninterrupted in an axial direction until a durable, rigid matrix of bone is formed throughout.

Figure 6A:
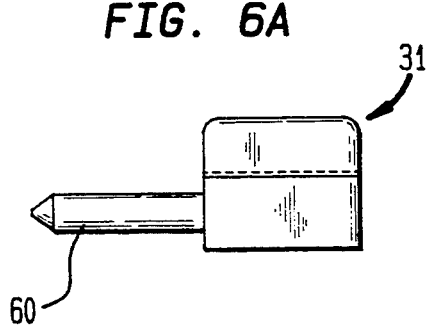
FIGS. 6A–6C are various views depicting another embodiment of a stabilizing member which may be utilized to secure the implant of the present invention to a neighboring vertebral body.
Figure 6B:
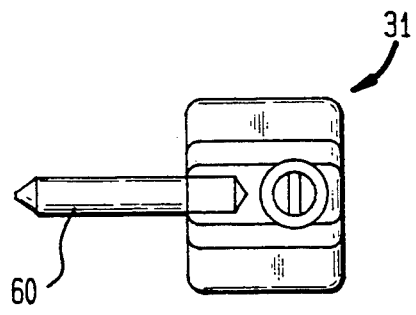
Figure 6C:
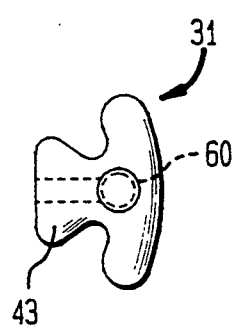

Although the stabilizing member depicted in FIGS. 4A–4C is preferred, it should be noted that many modifications are possible and that any suitable structure configured for selective positioning within the channels and adapted to lock the implant 10 to a vertebral body may be employed. An alternate embodiment is depicted in FIGS. 6A–6C and FIG. 7, in which like numerals are used to identify like elements. As seen in FIG. 6A–6C, modified stabilizing member 31 also includes a generally dovetail-shaped locking protrusion 43 that has diverging external surfaces 42 and 44. This locking protrusion 43 fits within the channels on the implant 10 in the same manner as before described with the preceding embodiment. A pin member 60 extends from the stabilizing member 31. The pin member 60 has a tapered point that allows the pin member 60 to be driven into bone.

Figure 7:
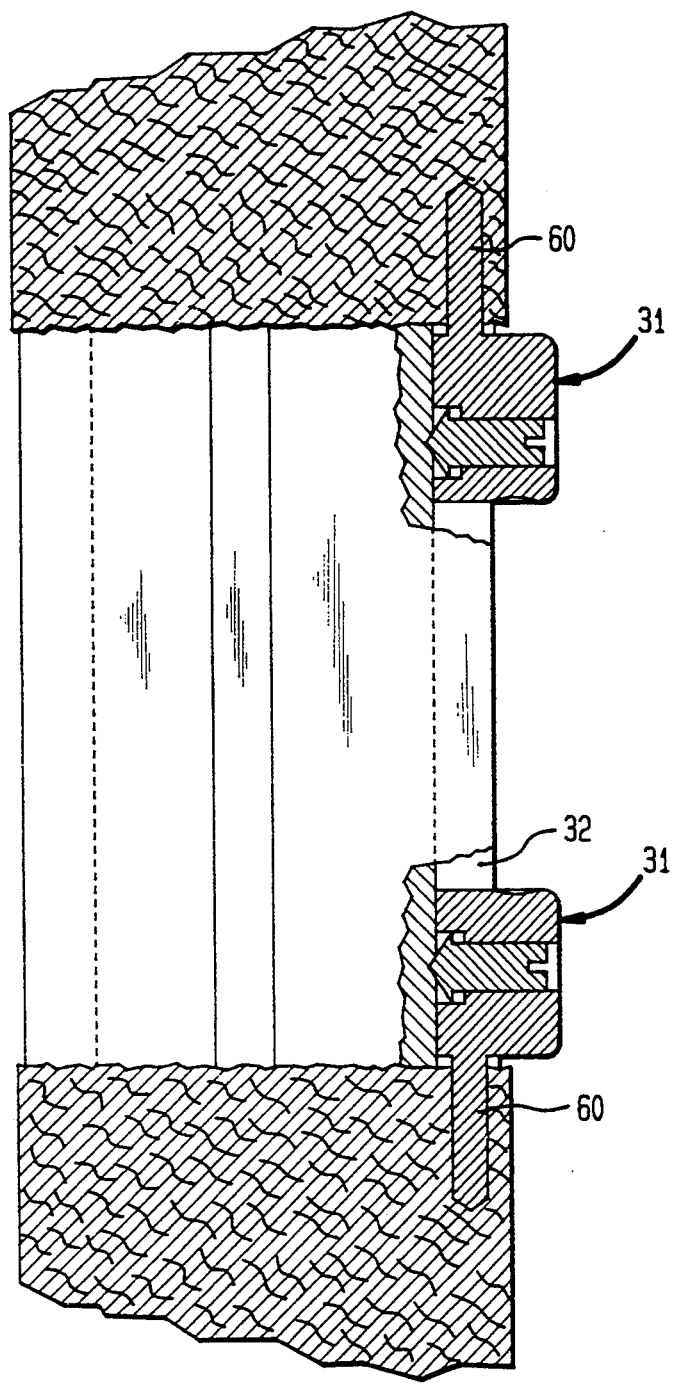
FIG. 7 is a cross-sectional view of the prosthesis vertebral body, wherein two stabilizing members such as those shown in FIGS. 6A–6C used to secure the prosthetic vertebral body to the surrounding vertebrae.

Referring to FIG. 7, in can be seen that once the stabilizing member 31 has been inserted into a channel 32 on the implant 10, the surgeon applies an impact force to the stabilizing member 31 until pin member 60 seats in the hard cortex bone of the vertebral body end plate. This provides the adjunct initial fixation between the stabilizing members 31 and the surrounding vertebral bone and may replace the need of bone screws as required in the previously described embodiments.

Figure 8B:
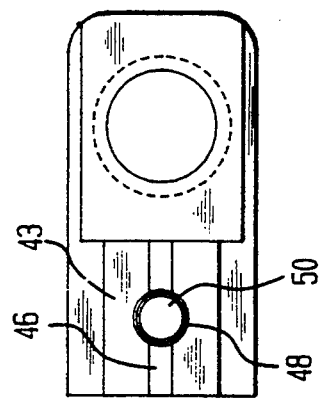
FIG. 8A and 8B show an alternate embodiment of the section of the stabilizing member that engages the prosthetic vertebral body.
Figure 8A:
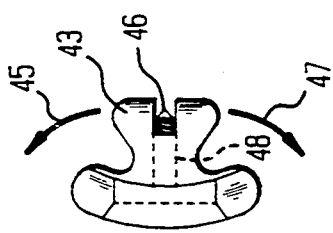

Referring to FIG. 8 there is shown an alternate embodiment to the locking protrusion 43 portion of the stabilizing member that could be used with either the embodiment of FIGS. 4A–4C or FIGS. 6A–6C. In the shown variation, an axial slot 46 is disposed within the locking protrusion 43. The axial slot 46 communicates with the screw hole 48 through which the screw 50 passes. As the locking screw 50 is driven through the screw hole 48 and into the material of the implant, the bulk of the advancing screw 50 spreads the axial slot 46 causing the shape of the locking protrusion 43 to change slightly and expand in the directions of arrows 45 and 47. The expansion of the locking protrusion 43 causes the locking protrusion 43 to create an interference fit with the channel on the implant in which the locking protrusion lay. This further acts to anchor the stabilizing member in one set position in regard to the implant.

Although a preferred embodiment of the present invention has been illustrated and described, it will be understood that various changes, adaptations, and modifications may be made by those persons having ordinary skill in the art to which the aforementioned invention pertains without departing from the spirit and scope of the invention. Accordingly, it is to be understood that the invention is not to be limited by the specific illustrated embodiment, but only by the scope of the appended claims.

We claim:

1. A vertebral body prosthetic device for replacing a surgically removed natural vertebral body, comprising:
   a vertebral body prosthesis dimensioned and arranged to be positioned between first and second separated natural vertebral bodies, said vertebral body prosthesis having a first end surface for engaging the first natural vertebral body, a second end surface substantially opposite said first end surface for engaging the second natural vertebral body, an external peripheral surface connecting said first and second surfaces, and at least one axially extending channel formed on said external peripheral surface along a length extending between said first end surface and said second end surface; and
   stabilizing means including axially extending plate means dimensioned and arranged to attach to one of said first and second natural vertebral bodies for securing said prosthetic vertebral body to said one of said first and second natural vertebral bodies, said stabilizing means being slidably positionable along said length of said at least one channel.

2. The device of claim 1, wherein said prosthesis is comprised of a rigid bio-compatible material.

3. The device of claim 2, wherein said material is porous.

4. The device according to claim 3, wherein said material has a bulk volume porosity of at least 60%.

5. The device according to claim 2, wherein said prosthesis is comprised of tantalum.

6. The device according to claim 1, wherein said at least one channel extends along an anterior portion of said external peripheral surface.

7. The device according to claim 1, wherein said external peripheral surface is a lateral surface of said prosthesis.

8. The device of claim 1, wherein said plate means comprises a first section slidably positionable within said at least one channel and a second section securable to one of said first and second natural vertebral bodies.

9. The device of claim 8, wherein said first section includes expanding means for locking said first section within said at least one channel in a set position.

10. The device of claim 9, wherein said at least one channel defines outwardly converging sidewall surfaces, and wherein said first section defines correspondingly diverging external surfaces dimensioned and arranged to permit sliding movement within said at least one channel when in a non-expanded condition.

11. The device of claim 10, wherein said expanding means includes an axial slot between said diverging surfaces and means insertable into said slot for moving said diverging external surfaces into said expanded condition thereby locking said diverging external surfaces with said converging sidewall surfaces.

12. The device of claim 8, wherein said second section of said rigid member includes at least one projecting pin member insertable into one of said first and second natural vertebral bodies.

13. The device of claim 8, wherein said second section of said plate means includes an upper and lower surface and defines a bore extending therethrough.

14. The device of claim 8, wherein said first section defines a screw hole extending therethrough, said screw hole being dimensioned and arranged to receive a threaded locking screw.

15. The device according to claim 14, wherein said locking screw is adapted to be selectively driven through said screw hole.

16. The device according to claim 15 further including a stopping means for preventing said locking screw from disengaging from said screw hole and for preventing said locking screw from extending out of said screw hole in a direction opposite said vertebral body prosthetic.

17. The device according to claim 15, wherein said vertebral body prosthetic is comprised of a material that is adapted to be penetrated by a portion of said locking screw that is driven through said screw hole, whereby a material of said vertebral body prosthetic envelops said portion of said locking screw.

18. The device according to claim 1, wherein at least one of said first and second end surfaces diverges at an acute angle relative to other one of said first and second end surfaces.

19. The device according to claim 1, wherein said first and second end surfaces each have a pattern of ridges and grooves defined thereon, said ridges being adapted to engage cancellous bone of said first and second natural vertebrae and said grooves being adapted to accommodate ingrowth of blood capillaries and bone tissue therefrom.

20. The device according to claim 1, wherein said at least one channel is adapted to retain bone graft material disposed therein, whereby said bone graft material facilitates ingrowth of bone into said at least one channel.

* * * * *